United States Patent [19]
Patnode et al.

[11] Patent Number: 5,143,091
[45] Date of Patent: Sep. 1, 1992

[54] MULTI-POSITION DRAPE FOR SURGERY ON A LIMB

[75] Inventors: Gregg A. Patnode; Robert L. Wheeler, both of St. Paul, Minn.

[73] Assignee: Minnesota Mining and Manufacturing Company, St. Paul, Minn.

[21] Appl. No.: 518,641

[22] Filed: May 9, 1990

[51] Int. Cl.⁵ .............................................. A61F 13/00
[52] U.S. Cl. ...................................... 128/853; 128/849
[58] Field of Search ................................ 128/849–856

[56] References Cited

U.S. PATENT DOCUMENTS

| | | | |
|---|---|---|---|
| 3,882,859 | 5/1975 | Ericson | 128/132 D |
| 3,942,523 | 3/1976 | Rudtke | 128/853 |
| 4,253,451 | 3/1981 | Solomon | 128/132 D |
| 4,378,794 | 4/1983 | Collins | 128/853 |
| 4,462,396 | 7/1984 | Wichman | 128/853 |
| 4,553,539 | 11/1985 | Morris | 128/854 |
| 4,598,458 | 7/1986 | McAllester | 128/853 |
| 4,869,271 | 9/1989 | Idris | 128/853 |
| 4,890,628 | 1/1990 | Jackson | 128/849 |
| 4,953,566 | 9/1990 | Garren | 128/849 |
| 4,974,604 | 12/1990 | Morris | 128/853 |

OTHER PUBLICATIONS

Advertisement for Convertors ® Arthroscopy Drape in Aorn Journal, Aug. 1987, vol. 46, No. 2, p. 263.

Primary Examiner—Mickey Yu
Assistant Examiner—Kerry Owens
Attorney, Agent, or Firm—Gary L. Griswold; Walter N. Kirn; Dale A. Bjorkman

[57] ABSTRACT

Surgical drapes for isolating the knee or other portion of a limb of a patient in surgery wherein the drape comprises a sheet having two fenestrations in elastomeric material to receive the limb of the patient. These fenestrations are located on the drape so that they normally lie in a generally common plane when the drape is placed on a flat surface. Due to the location of the fenestrations, the drape itself has a low profile with respect to the operative site and readily adapts to different limb positions that may be encountered during surgery. This advantage is particularly important in drapes comprising a fluid collection pouch.

12 Claims, 8 Drawing Sheets

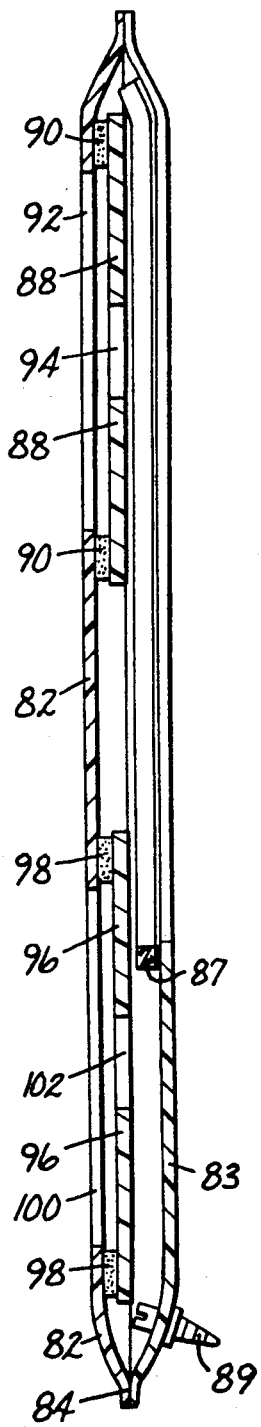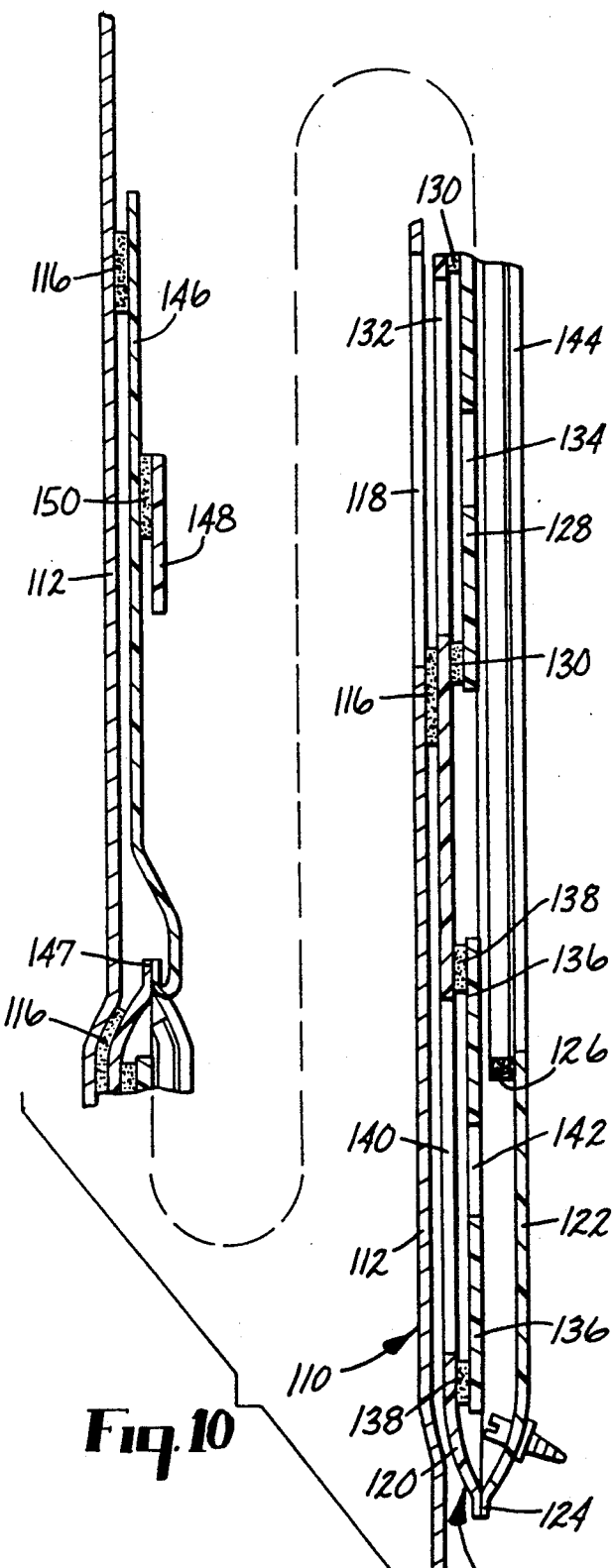
Fig. 9
Fig. 10

MULTI-POSITION DRAPE FOR SURGERY ON A LIMB

FIELD OF INVENTION

The present invention relates to surgical drapes, and more particularly to surgical drapes for isolating a limb.

BACKGROUND OF THE INVENTION

Surgical drapes having elastomeric portions to help isolate parts of the body during surgery and to protect against infection have been available for some time.

U.S. Pat. No. 3,882,859 to Ericson discloses an elastic fenestrated drape that is essentially a non-adhesive incise drape. The drape described in this patent is laid over the preprepared surgical site, and the surgeon cuts through the elastomer to expose the operative site. The elastomer may be stretched open to enhance access to the site.

The "Converters® Arthroscopy Drape" with pouch, catalog number A9185T available from Baxter Health Care Corp., Deerfield, Ill., is a one piece drape with an attached pouch. The drape is provided with an elastomeric section having a fenestration that surrounds the leg above the knee. The pouch is an inverted pyramid or cone in shape, with an exit port for fluid provided at the apex of the pouch. A second elastomeric section having a fenestration to receive the lower portion of the leg is provided on the opposite side of the pouch from the first elastomeric section. Because the pouch is attached on opposite sides to the leg, the stability and drainability of this pouch is greatly dependent on the positioning of the leg.

Drapes used in surgery on a limb, and particularly knee arthroscopy surgeries, in the past have been cumbersome to use, got in the way of the surgical team or were not adaptable to the different knee positions that may be used in surgery.

SUMMARY OF THE INVENTION

The present invention is drawn to a surgical drape for isolating the knee or other portion of a limb of a patient in surgery wherein the drape comprises a sheet having two fenestrations in elastomeric material to receive the limb of the patient. These fenestrations are located on the drape so that they normally lie in a generally common plane when the drape is placed on a flat surface. Due to the location of the fenestrations, the drape itself has a low profile with respect to the operative site and readily adapts to different limb positions that may be encountered during surgery. This advantage is particularly important in drapes comprising a fluid collection pouch.

In use, the operative limb of the patient is placed through the two fenestrations. The first fenestration is pulled to a location above the operative site on the limb, and the second fenestration is pulled to a location below the operative site on the limb. The two fenestrations in the elastomeric material conform to the skin of the patient and form an effective seal to isolate the operative site.

BRIEF DESCRIPTION OF THE DRAWINGS

FIG. 9 is a cross-section of the drape of FIG. 7 taken along line 9—9 showing both fenestrations;

FIG. 10 is a cross-section of a drape similar to the drape shown in FIG. 5;

DETAILED DESCRIPTION OF THE DRAWINGS

Figure 1:
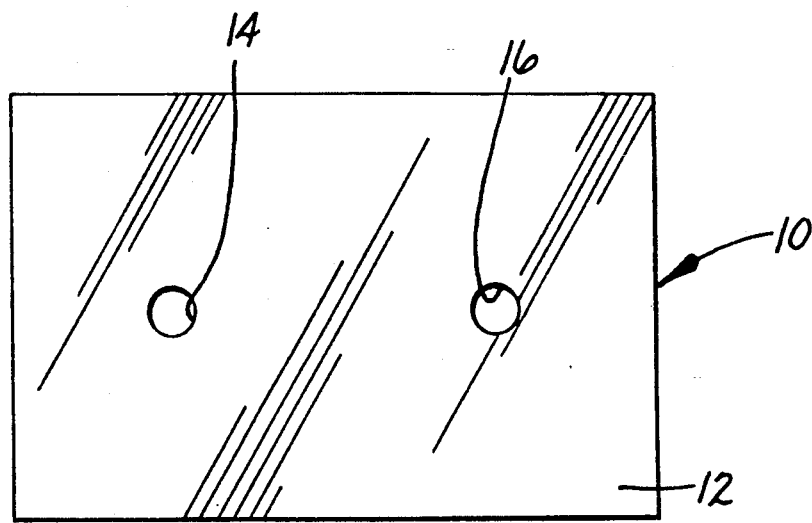
FIG. 1 is a plan view of a drape of the present invention comprising a single elastomeric sheet.

FIG. 1 is a plan view of a drape of the present invention wherein drape 10 comprises elastomeric piece 12 that is provided with first fenestration 14 and second fenestration 16. In use, the operative limb of the patient (not shown) is placed through first fenestration 14, entering from a position below the plane of drape 10. The operative limb is then placed through second fenestration 16, entering second fenestration 16 from a position above the plane of drape 10. First fenestration 14 is pulled to a location above the operative site on the limb, and second fenestration 16 is pulled to a location below the operative site on the limb. The operative site is thus located between first fenestration 14 and second fenestration 16 above the plane of drape 10. Fenestrations 14 and 16 in elastomeric piece 12 conform to the skin of the patient and form an effective seal to isolate the operative site.

Figure 2:
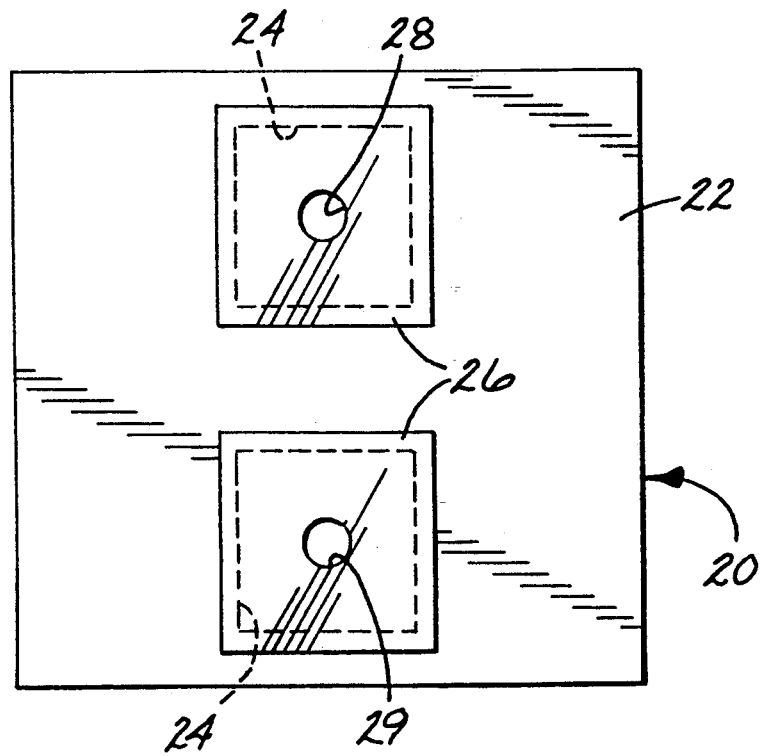
FIG. 2 is a plan view of a drape comprising two separate elastomeric portions in a main sheet.

FIG. 2 is a plan view of an alternative embodiment of the drape of the present invention. Drape 20 comprises main sheet 22 that is made from any flexible, substantially fluid impervious sheet material. Main sheet 22 is provided with two apertures 24, shown in phantom. Elastomeric pieces 26 are attached to main sheet 22 over the area generally corresponding to apertures 24. Elastomeric pieces 26 are provided with first fenestration 28 and second fenestration 29 that will receive the limb of the patient as described in detail in the discussion of FIG. 1.

Figure 3:
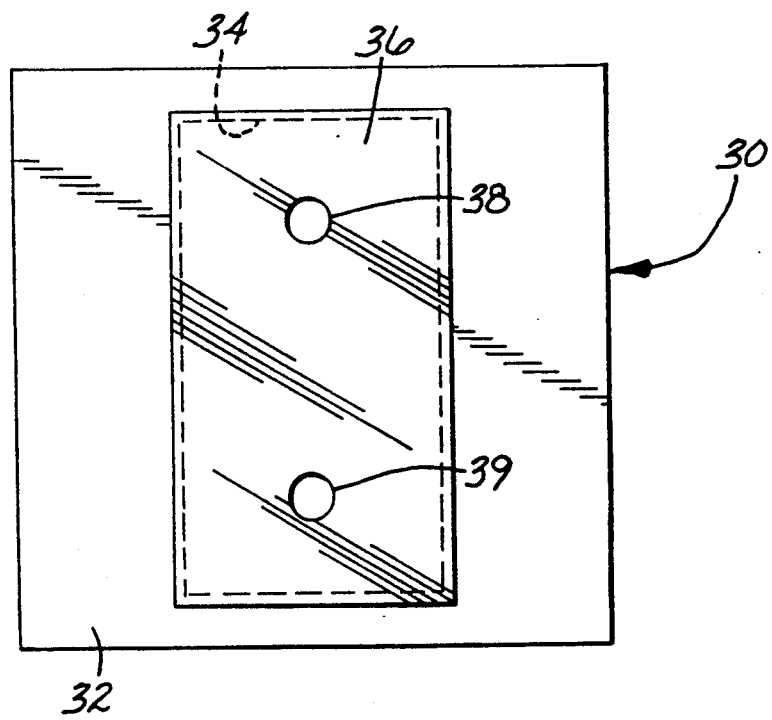
FIG. 3 is a plan view of a drape having a single elastomeric portion on a main sheet.

FIG. 3 is a plan view of drape 30, which comprises main sheet 32 having aperture 34 (shown in phantom). A single elastomeric piece 36 is attached to main sheet 32 around the edges of aperture 34. Elastomeric piece 36 is provided with first fenestration 38 and second fenestration 39 for receiving a patient's limb as described in detail in the discussion of FIG. 1. Both fenestrations 38 and 39 are located in the region of the elastomeric piece 36 bounded by the attachment to the main sheet 32.

Figure 4:
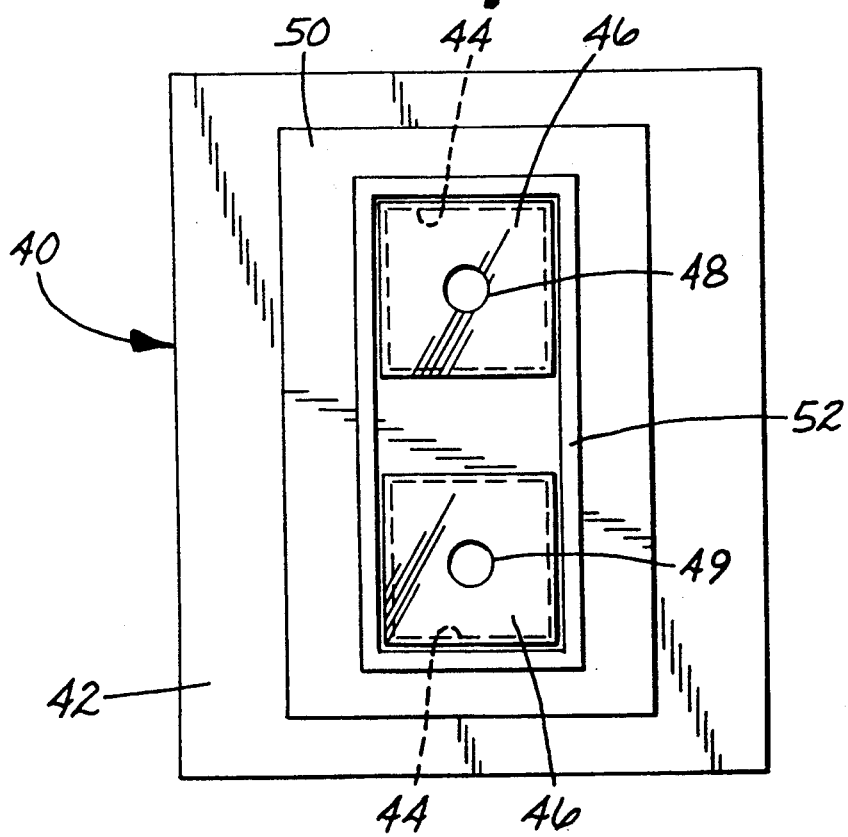
FIG. 4 is a plan view of a drape having two elastomeric portions and fluid absorbent features.

FIG. 4 is a plan view of drape 40 comprising main sheet 42 provided with two apertures 44 (shown in phantom). Elastomeric pieces 46 are attached to main sheet 42 around the edges of apertures 44. Elastomeric pieces 46 are provided with first fenestration 48 and second fenestration 49 for receiving a limb. Absorbent pad 50 is attached to main sheet 42 and generally surrounds elastomeric pieces 46 for receiving and absorbing fluids of surgery. Absorbent pad 50 is made from any fluid absorbent material, such as materials used in regular or disposable diapers or the like. Additional absorbent cuff 52, made from the same of a different absorbent material as absorbent pad 50, is provided to surround elastomeric pieces 46 for extra absorbency of surgical fluids.

Figure 5:
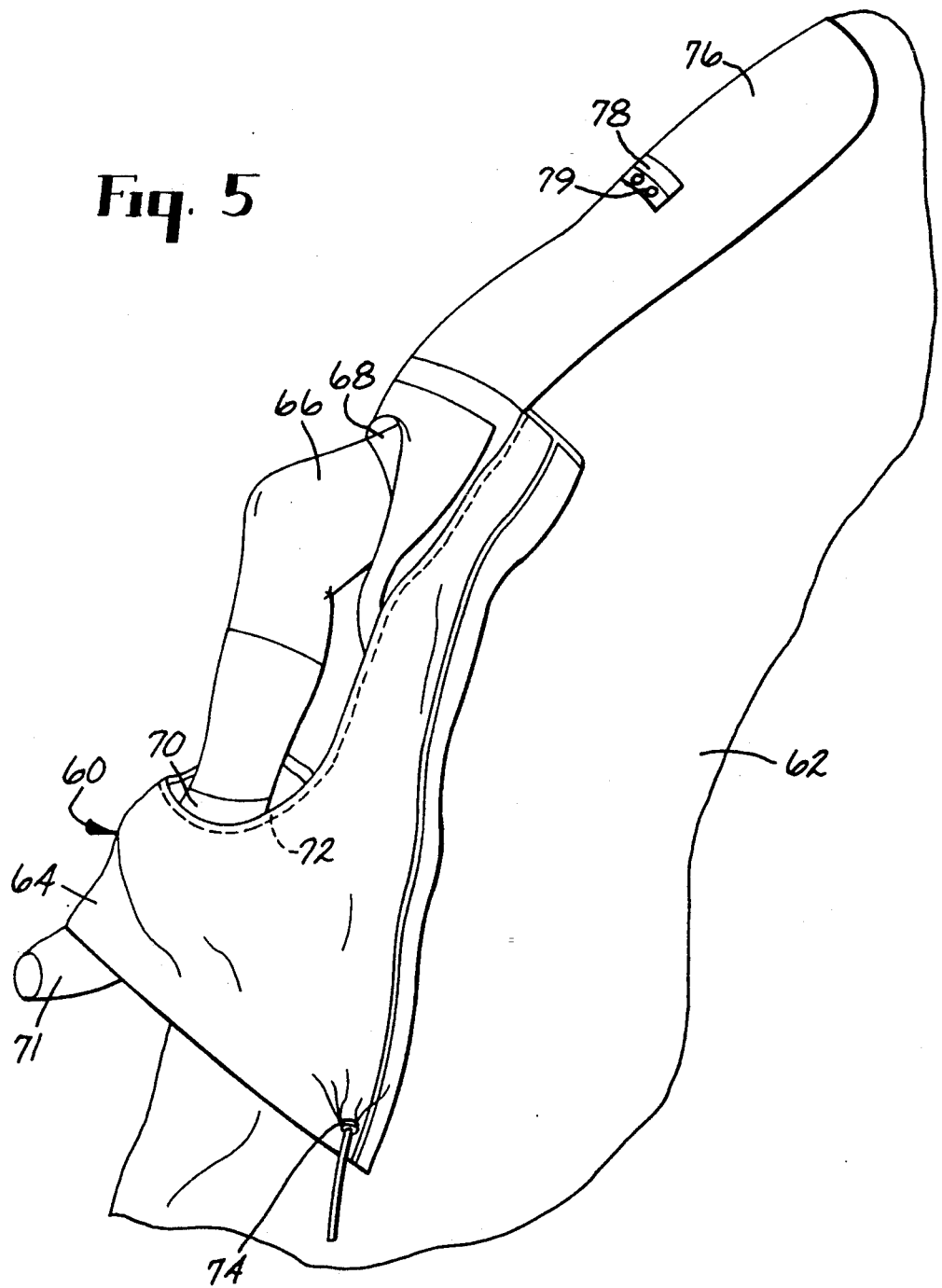
FIG. 5 is a perspective side view of a drape in position on a patient's leg.

FIG. 5 is a perspective side view of drape 60 of the present invention in position on a patient. Drape 60 is provided with main sheet 62 and pouch 64. Patient's leg 66 extends through first elastomeric piece 68 and extends again through second elastomeric piece 70. The knee portion of leg 66 is within the operative field, and foot 71 is outside the operative field but still within the sterile field. Leg 66 thus can be manipulated using foot 71 while maintaining the sterility of operative personnel. Pouch 64 substantially surrounds elastomeric piece 62 on three sides to collect fluids of surgery. Spacing means 72 is an open cell foam provided on the inner surface of the outer edge of pouch 64 to prevent closure of pouch 64 and spillage of surgical fluids. Port 74 is provided in pouch 64 to allow drainage of surgical fluids collected therein. A tough reinforcement sheet 76 is provided above pouch 64 and is attached to main sheet 62 to provide a convenient place for clamping surgical instruments. Utility flap 78 is an additional portion of tough material attached to tough reinforcement sheet 76. Utility flap 78 provides a convenient projection on which surgical instruments may be clamped. Holes 79 are provided in utility flap 78 through which tubing or cords may be passed or tied.

Figure 6:
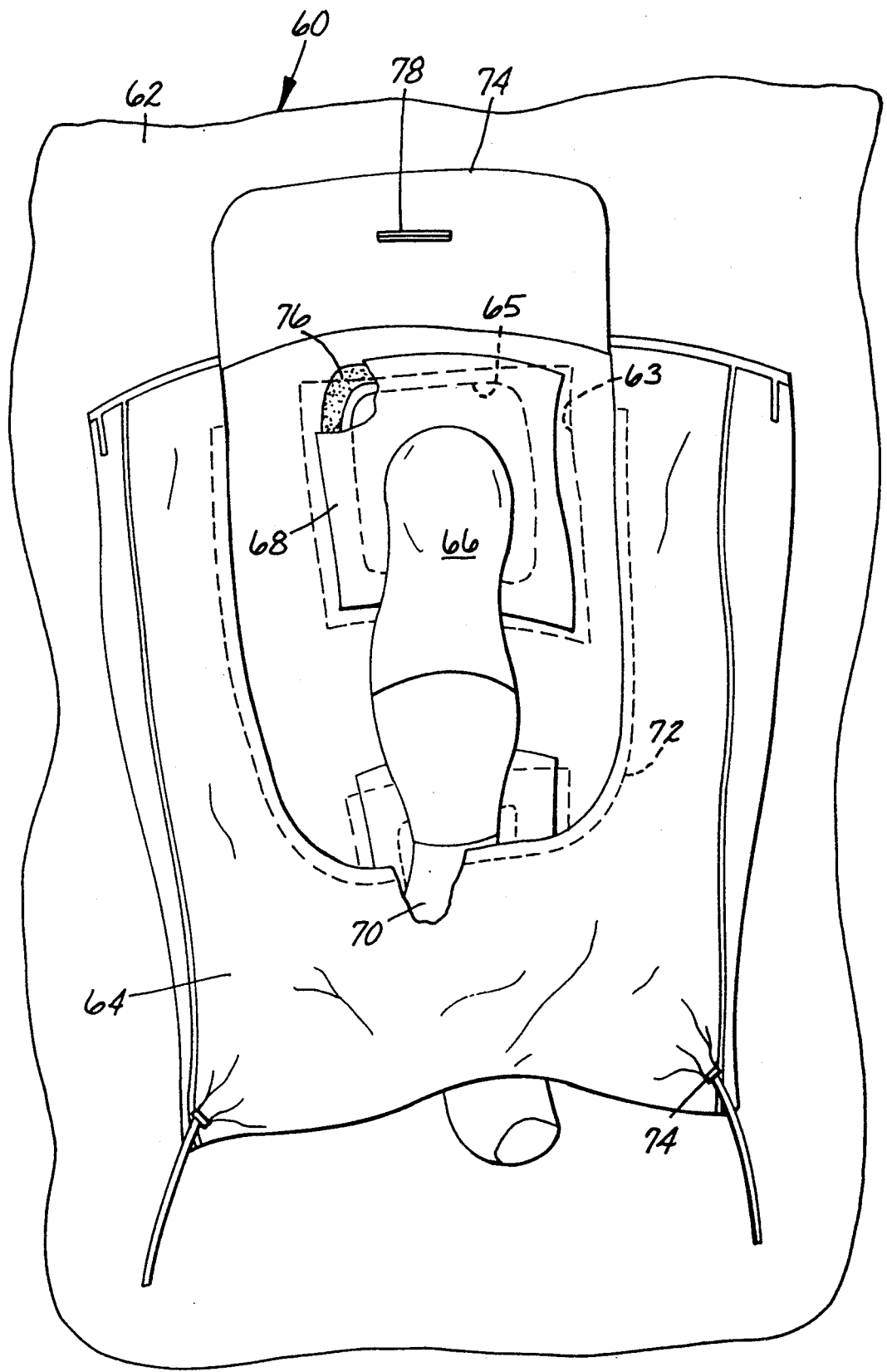
FIG. 6 is a perspective front view of the drape of FIG. 5.

FIG. 6 is a perspective front view of surgical drape 60 as shown in FIG. 5. Main sheet 62 is provided with main sheet aperture 63 (shown in phantom) and pouch 64 is provided with pouch aperture 65, both apertures accommodating extension of leg 66 therethrough. Pouch 64 is attached to main sheet 62 at the periphery of main sheet aperture 63 so that pouch aperture 65 aligns with main sheet aperture 63. First elastomeric piece 68 is adhered along the edges of pouch aperture 65 to pouch 64 with adhesive 76. Second elastomeric piece 70 is similarly adhered to pouch 64.

Figure 7:
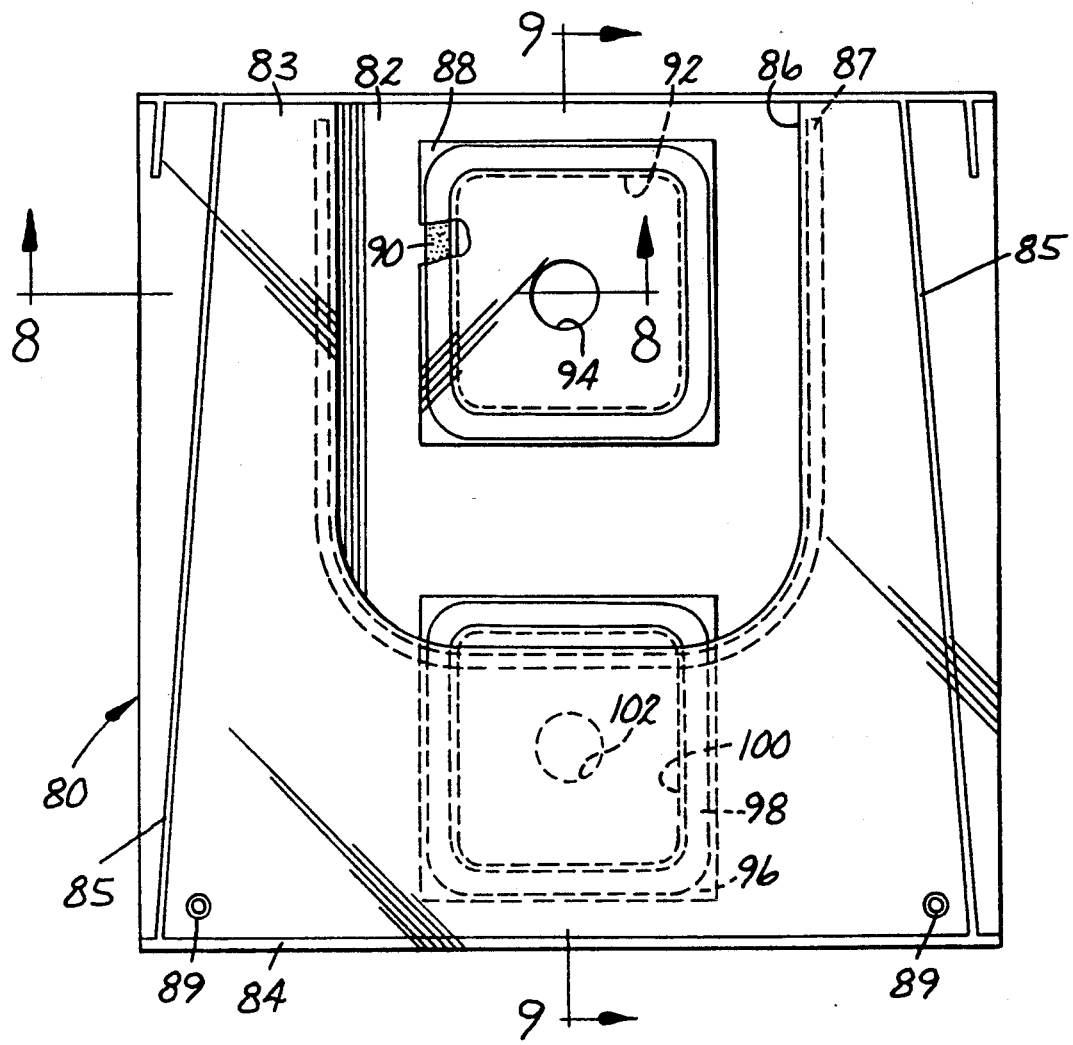
FIG. 7 is a plan view with portions shown in phantom of a drape of the present invention comprising a pouch.

FIG. 7 is a plan view of a pouch drape 80, which is a drape consisting entirely of a pouch construction without an additional main sheet, with portions shown in phantom and portions cut away. Pouch drape 80 is formed by heat sealing inner wall 82 to outer wall 83 along bottom seal 84 and side heat seals 85. Side heat seals 85 are preferably made at converging 85° angles from bottom seal 83 to enhance efficient collection and drainage of surgical fluids. First elastomeric piece 88 is adhered using adhesive 90 to inner wall 82 along the edges of first aperture 92 in inner wall 82. First elastomeric piece 88 is provided with first fenestration 94 to receive the limb of the patient. Similarly, second elastomeric piece 96 is adhered using adhesive 98 to inner wall 82 in an area generally corresponding to second aperture 100. Second elastomeric piece 96 is provided with second fenestration 102 to receive the lower portion of the limb of the patient. Outer wall 83 is cut out along U-shaped cutout line 86 to provide easier access to the knee of the patient without interference from outer wall 83. Thus, when pouch drape 80 is placed on a flat surface with inner wall 82 down, first fenestration 94 is uncovered by outer wall 83 and second fenestration 102 is covered by outer wall 83. Spacing means 87 is attached to the inner surface of outer wall 83 along the periphery of cutout line 86 in order to prevent the pouch from closing on itself and spillage of surgical fluids.

Figure 8:
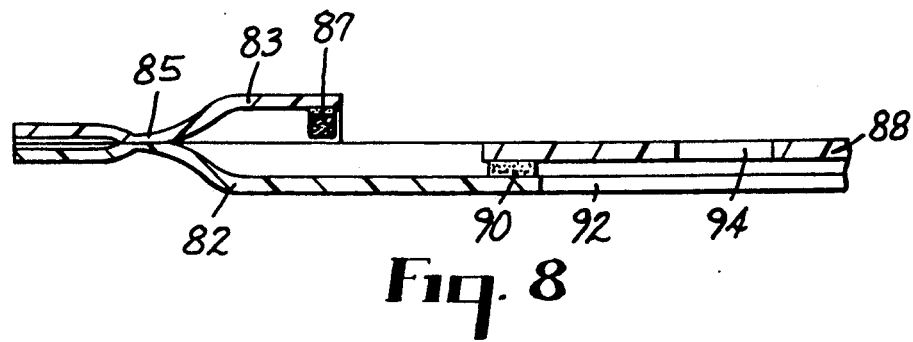
FIG. 8 is a cross-section of the drape of FIG. 7 taken along line 8—8.

FIG. 8 is a cross-sectional view of the drape of FIG. 7 taken along lines 8—8. Outer wall 83 is heat sealed along side heat seal line 85 to inner wall 82. Spacing means 87, which is an open cell foam that will allow flow of surgical fluids therethrough, is adhered to the inner surface of outer wall 83 along the edge of U-shaped cutout line 86. First elastomeric piece 88 is adhered to inner wall 82 using adhesive 90 in the area generally corresponding to first aperture 92. First fenestration 94 is generally centrally located in first elastomeric piece 88.

FIG. 9 is a cross-sectional view of the drape of FIG. 7 taken along the lines 9—9. First aperture 92 and second aperture 100 are provided in inner wall 82 to receive the limb as it extends through the general region of the pouch by entering through first aperture 92 and exiting through second aperture 100. To inner wall 82 at the general area of first aperture 92 is adhered first elastomeric piece 88 using adhesive 90. First elastomeric piece 88 is provided with first fenestration 94. Similarly, second elastomeric piece 96, provided with second fenestration 102, is adhered using adhesive 98 to inner wall 82 in the area generally corresponding to second aperture 100. Outer wall 83 is provided with port 89 for the convenient removal of surgical fluids and spacing means 87 to prevent closure of the pouch.

FIG. 10 is a cross-sectional view of a drape having a main sheet such as is shown in FIG. 5. Drape 110 is provided with main sheet 112 having pouch 114 attached thereto using pouch attachment adhesive 116 Main sheet 112 is provided with main sheet aperture 118 for receiving the limb of the patient (not shown). Pouch 114 is formed by heat sealing inner wall 120 to outer wall 122 on three sides. One of these heat seals, bottom heat seal 124, is shown. Spacing means 126 is provided to prevent closure of the pouch and spillage of surgical fluids. First elastomeric piece 128 having first fenestration 134 therein is adhered to the inner wall 120 of pouch 114 using adhesive 130. This first elastomeric piece 128 is adhered around the edges of first aperture 132 provided in inner wall 120 so that the limb of the patient may extend through main sheet 112, inner wall 120 of pouch 114 and first elastomeric piece 128. Similarly, second elastomeric piece 136 having second fenestration 142 therein is adhered to inner wall 120 using adhesive 138. This second elastomeric piece 136 is adhered to inner wall 120 around the edges of second aperture 140 provided in inner wall 120. A U-shaped cut is made in outer wall 122 of pouch 114 to provide U-shaped opening 144. The excess material thus provided by this cut is folded up to provide tough reinforcement portion 146. Tough reinforcement portion 146 is attached to pouch 114 by heat seal 147, and additionally is preferably adhered to main sheet 112. Utility flap 148 is attached to U-shaped reinforcement 146 using adhesive 150 to provide an additional member for attachment of surgical tubing and clamping of surgical instruments.

Figure 11:
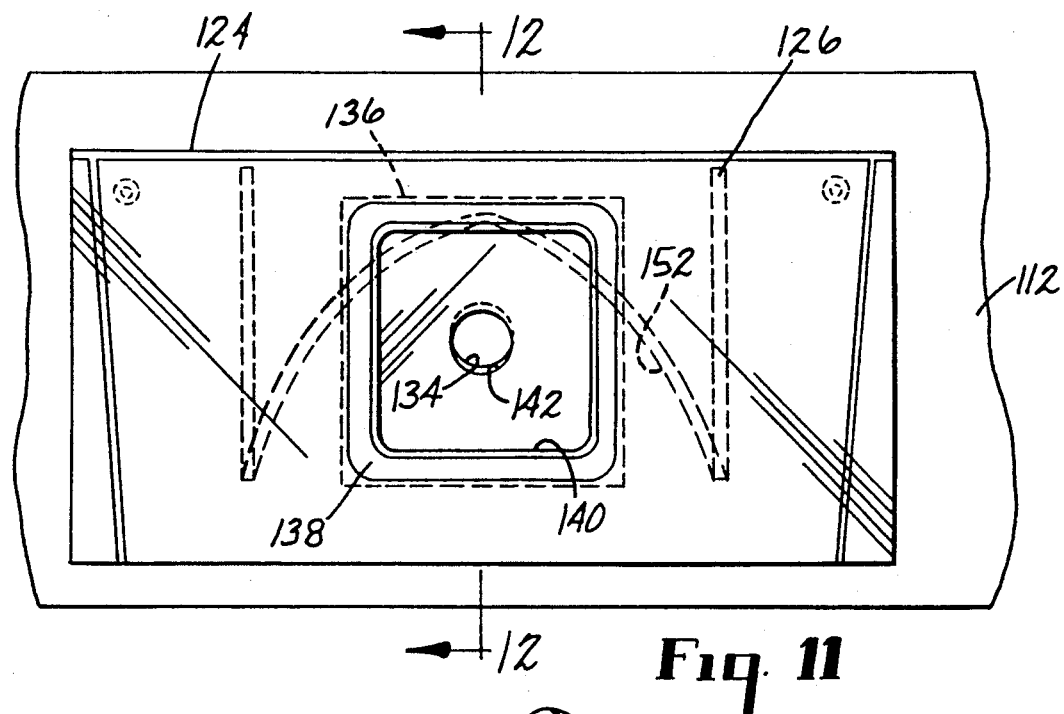
FIG. 11 is a plan view of the drape of FIG. 10 in a folded configuration, with portions shown in phantom.

FIG. 11 is a top view of the drape of FIG. 10 in a folded configuration with portions shown in phantom. The drape is folded in such a way that first fenestration 134 with second fenestration 142 and the drape can be easily placed on the patient by pushing the limb through both fenestrations simultaneously. This view shows the edge 152 of U-shaped opening 144 shown in FIG. 10.

Figure 12:
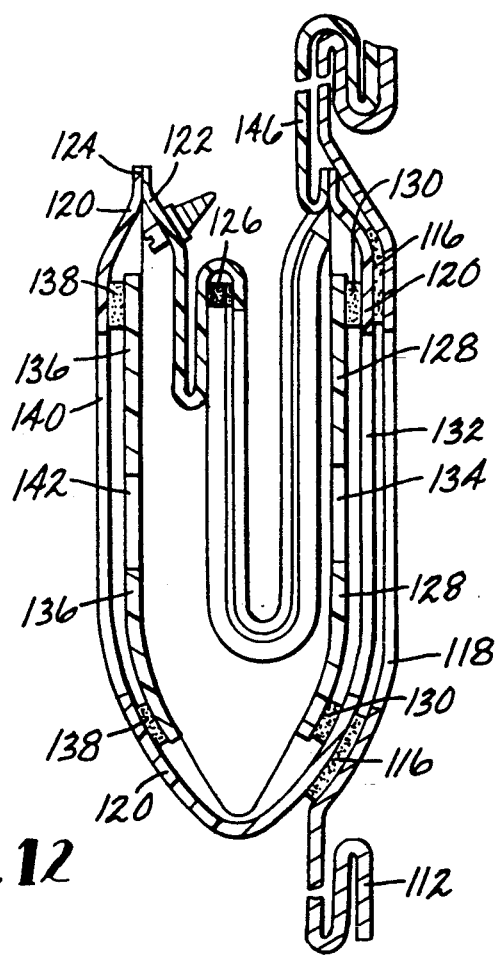
FIG. 12 is a cross-sectional view of the folded drape of FIG. 11.

FIG. 12 is a cross-sectional view of a folded drape of FIG. 11. Apertures 142 and 134 align with no material located between them, so that the limb of the patient may be pushed through both apertures simultaneously.

Figure 13:
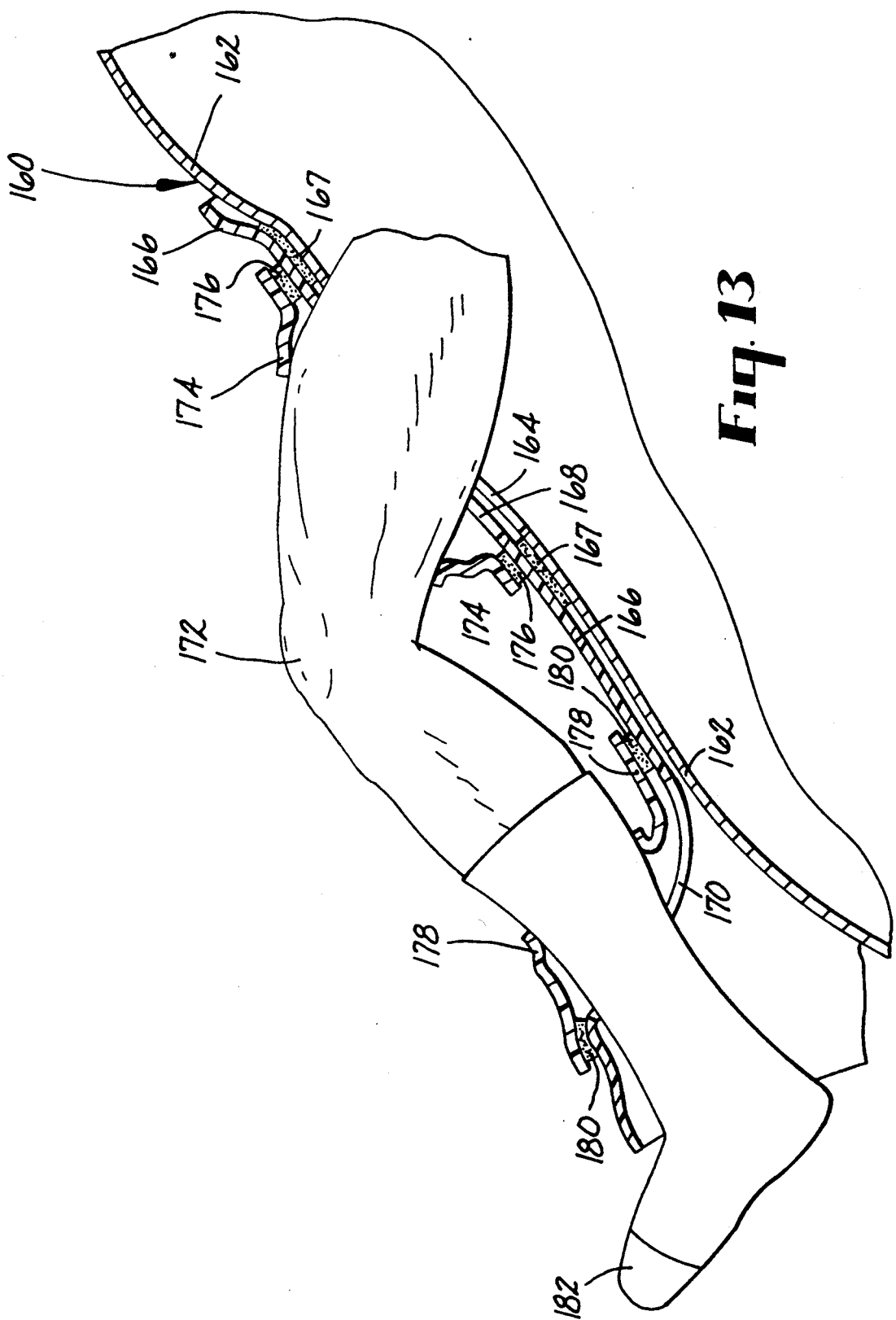
FIG. 13 is a cross-sectional view of an alternative embodiment of the drape of the present invention.

FIG. 13 is an alternate embodiment to the present invention having no pouch, shown partly in section, wherein drape 160 is provided with main sheet 162 having main sheet aperture 164 for receiving patient's limb 172. Second sheet 166 is attached to main sheet 162 in the area surrounding main sheet aperture 164 by adhesive 167. Second sheet 166 is provided with first aperture 168 in the area generally corresponding to main sheet aperture 164, and second aperture 170 distally removed from first aperture 168 for receiving the lower portion of a patient's limb 172. First elastomeric portion 174 is attached to second sheet 166 in the area corresponding to first aperture 168 by adhesive 176. First elastomeric portion 174 is provided with a fenestration for receiving patient's limb 172. Second elastomeric portion 178 is similarly attached to second sheet 166 in the area corresponding to second aperture 170 by adhesive 180, and is also provided with a fenestration for receiving patient's limb 172. As in the drape of FIG. 5, limb 172 thus can be manipulated using foot 182 while maintaining the sterility of operative personnel. In contrast to the drape shown in FIG. 3, first elastomeric portion 174 having a fenestration is located in the region bounded by the attachment of second sheet 166 to main sheet 162, while second elastomeric portion having a fenestration is located in the region not bounded by the attachment of second sheet 166 to main sheet 162.

Detailed Description of the Presently Preferred Embodiments

Drapes prepared in accordance with the present invention may be adapted in size and configuration as appropriate to their particular use. The two fenestrations in the elastomeric material for receiving the limb of the patient may vary in size and spacing as required for the limb that will be operated on and the procedure to be performed. Because these fenestrations are surrounded by elastomeric material that will allow stretching to accommodate the limb of a patient, these fenestrations may be referred to as "elastomeric fenestrations". It is envisioned that the drapes of the present invention will be especially useful for the knee arthroscopy procedure performed on adult patients. It has been determined that a particularly preferred spacing between fenestrations is about 430 mm. from center to center of the fenestrations. This spacing could of course vary with the size of the limb to be operated on, but because the fenestrations are in elastomeric material that conforms to the skin of the patient and securely holds the drape in place, a single selected spacing of fenestrations on the range of 300-500 mm. will satisfactorily accommodate most size limbs. Similarly, the diameters of the fenestrations may vary depending on the size of the limb to be accommodated. In drapes to be used for adult knee arthroscopy procedures, the first fenestration generally has a diameter of about 55 to 75 mm., and preferably about 65 mm., to accommodate the upper region of the leg. The second fenestration generally has a diameter of about 35 to 55 mm., and preferably about 45 mm. to accommodate the lower portion of the leg. As in the selection of spacing above, because the fenestrations are in elastomeric material that conforms to the patient, a single selected set of fenestration diameters will satisfactorily accommodate most size limbs.

When the drape is provided with a pouch, the pouch preferably has one or more ports for draining the collected surgical fluids. Surprisingly, it has been discovered that these ports are preferably located on the outer wall of the pouch to provide more effective drainage. As the pouch fills with fluids, the walls distend and change the direction that the port points. When the port is located on the inner wall of the pouch, there is a tendency for the port to point up as the pouch fills with a resulting impedance of proper drainage. Ports located on the outer wall of the pouch, in contrast, tend to point down as the pouch fills and the pouch drains properly.

The elastomeric material used for making portions of the drape of the present invention may be selected from any sheet material that possesses elastomeric recovery properties. Particularly preferred materials will substantially recover from at least about an 800 percent elongation. An example of a particularly preferred material is "Krato ® rubber" commercially available from the Shell Chemical Company, Houston, Tex. which is a block copolymer of styrene and butadiene.

Parts of the drape of the present invention that are not elastomeric may be made from any flexible fluid resistant or substantially fluid impervious material. These parts include the main sheet, second sheet, pouch and any reinforcing portions that may be provided on the drape. Particularly preferred materials for use as the main or second sheet are the non-woven fabric/plastic film laminate materials commonly used in the surgical drape art. Such materials are disclosed, for example, in U.S. Pat. No. 3,809,077. The sheet may alternatively be fabricated from a fabric that has been rendered fluid resistant or substantially fluid impervious by application of a chemical treatment. Totally fluid impervious materials, such as plastics including polyethylene, polyester, polyamide, polyvinyl chloride and the like may also be used as sheet materials.

The pouch is preferably constructed from totally fluid impervious materials such as the plastics listed above to minimize the likelihood of leaks. Fabric/plastic film laminates may be used, but are not preferred because fluids wick in the fabric layer and can result in messy containment problems.

The spacing means could be constructed of an open cell foam, filamentary structure or other material that provides for relatively free flow of surgical fluids therethrough. Sheet stock of open cell polyurethane foam (commercially available as "Type P-10 polyurethane foam" from Illbruck Company, Minneapolis, Minn.) is particularly preferred.

The elastomeric sheet is attached to the main sheet by adhesive, heat seal, solvent welding, sonic welding, or any other appropriate technique depending on the selection of material. Similarly, the pouch or second sheet is attached to both the main sheet and the elastomer by any such appropriate method. The spacing means is also attached in a manner consistent with appropriate methods depending on the selection of means as described above. For example, when the spacing means is a rod, wire or other such mechanical stiffening agent, the spacing means may be enveloped within a fold in the pouch material that is secured to itself by heat seal, adhesive, or the like. When the spacing means is a foam or fibrous material, the spacing means may be attached using any of the above described methods depending on the particular selection of materials.

We claim:

1. A surgical drape comprising
a main sheet provided with a main sheet aperture,
and a pouch for collecting surgical fluids, said pouch comprising an inner wall and an outer wall, said inner wall having an elastomeric first fenestration and an elastomeric second fenestration, said fenestrations being adapted to receive a limb therethrough,
the inner wall of said pouch being attached to said main sheet at the edges of the aperture such that the aperture and the first fenestration align, and
wherein said first and second fenestrations normally lie in a generally common plane when the drape is placed on a flat surface.

2. The surgical drape of claim 1 wherein said fenestrations are provided in a single piece of elastomeric material.

3. The surgical drape of claim 1 wherein said fenestrations are provided in two separate pieces of elastomeric material.

4. The surgical drape of claim 1 wherein said first fenestration has a diameter of about 55 to 75 mm. and said second fenestration has a diameter of about 35 to 55 mm.

5. The surgical drape of claim 1 wherein said first fenestration has a diameter of about 65 mm. and said second fenestration has a diameter of about 45 mm.

6. The surgical drape of claim 1 wherein said first fenestration and said second fenestration are located about 300-500 mm. apart.

7. The surgical drape of claim 1 wherein said first fenestration and said second fenestration are located about 430 mm. apart.

8. The surgical drape of claim 1 wherein said outer wall of the pouch is shaped such that when the drape is placed on a flat surface with the inner wall down, the first fenestration is uncovered and the second fenestration is covered by the outer wall.

9. The surgical drape of claim 1 wherein the pouch is provided with at least one port for drainage of surgical fluids.

10. The surgical drape of claim 7 wherein at least one port is located in the outer wall of the pouch.

11. The surgical drape of claim 1 wherein the pouch is formed by heat sealing the inner wall to the outer wall by a bottom heat seal line and two side heat seal lines.

12. The surgical drape of claim 1 wherein the side heat seal lines are formed at converging angles of about 85° with respect to the bottom heat seal.

* * * * *